United States Patent
Fan et al.

(10) Patent No.: US 7,678,051 B2
(45) Date of Patent: Mar. 16, 2010

(54) PANORAMIC ELASTICITY ULTRASOUND IMAGING

(75) Inventors: Liexiang Fan, Sammamish, WA (US); Patrick Von Behren, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 733 days.

(21) Appl. No.: 11/237,204

(22) Filed: Sep. 27, 2005

(65) Prior Publication Data
US 2007/0073145 A1 Mar. 29, 2007

(51) Int. Cl.
*A61B 8/00* (2006.01)

(52) U.S. Cl. .................. 600/438; 600/437; 600/443; 600/440; 600/441

(58) Field of Classification Search ............ 600/437, 600/441, 443, 453, 463, 438
See application file for complete search history.

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,293,870 A | 3/1994 | Ophir et al. | |
| 5,782,766 A | 7/1998 | Weng et al. | |
| 5,910,114 A | 6/1999 | Nock et al. | |
| 6,503,201 B1 | 1/2003 | Liu et al. | |
| 6,508,768 B1 | 1/2003 | Hall et al. | |
| 6,558,324 B1 | 5/2003 | Von Behren et al. | |
| 6,572,549 B1 | 6/2003 | Jong et al. | |
| 6,641,536 B2 * | 11/2003 | Hossack et al. | 600/443 |
| 6,730,031 B2 | 5/2004 | Liu et al. | |
| 2006/0173320 A1 * | 8/2006 | Radulescu | 600/438 |
| 2008/0188744 A1 | 8/2008 | Fan et al. | |

* cited by examiner

*Primary Examiner*—Brian Casler
*Assistant Examiner*—John F Ramirez

(57) ABSTRACT

Using compression, tissue elasticity data from two or more different fields of view is acquired. Since different amounts of compression may be used for the different fields of view, the dynamic range of the elasticity data is updated. A panoramic elasticity image is generated from the updated elasticity data of multiple fields of view. A panoramic elasticity image represents the combined fields of view for the elasticity data.

9 Claims, 2 Drawing Sheets

PANORAMIC ELASTICITY ULTRASOUND IMAGING

BACKGROUND

The present embodiments relates to panoramic ultrasound imaging. Panoramic images are generated for B-mode and Doppler information. U.S. Pat. Nos. 5,782,766, 5,910,114, 6,503,201, 6,572,549, 6,730,031, and 6,641,536 describe some methods to generate panoramic images. Relative motion between adjacent frames is detected. The frames are assembled based on the relative motion into an extended field of view.

Another ultrasound imaging mode is elasticity imaging. U.S. Pat. Nos. 5,107,837, 5,293,870, 5,178,147, and 6,508,768 describe methods to generate elasticity images using the relative tissue displacement between adjacent frames. Strain, strain rate, modulus, or other parameters corresponding to tissue displacement are detected for generating an elasticity image. U.S. Pat. No. 6,558,324 describes methods to represent elasticity using color coding.

BRIEF SUMMARY

By way of introduction, the preferred embodiments described below include methods, instructions and systems for panoramic elasticity imaging. Using tissue compression, elasticity data from two or more different fields of view is acquired. Since different amounts of compression may be used for the different fields of view, the dynamic range of the elasticity data is updated. A panoramic elasticity image represents the combined fields of view for the elasticity data.

In a first aspect, a method is provided for elasticity ultrasound imaging. First elasticity data is acquired with ultrasound for a first region corresponding to a first position of a transducer. Second elasticity data is acquired with ultrasound for a second region corresponding to a second position of the transducer. The second position and second region are different from the first position and first region, respectively. An image represents both the first and second regions. The image is generated a function of the first and second elasticity data.

In a second aspect, a computer readable storage medium has stored therein data representing instructions executable by a programmed processor for extended field of view ultrasound imaging. The instructions are for generating a panoramic tissue elasticity image.

In a third aspect, a method is provided for extended field of view ultrasound imaging with elasticity or other types of data, such as B-mode. Relative displacement between frames of data is determined. For example, a primary displacement is determined by correlation between two or more frames. The primary displacement is decomposed into first (lateral direction) and second (axial direction) displacements. If the first displacement is greater than the second displacement, the two or more frames are combined as a function of the primary displacement. An alternative implementation is to separately compute the mean correlation in first direction, namely first correlation, and compute the mean correlation in second direction different from the first direction, namely second correlation. A displacement is chosen in the first direction and two or more frames are combined as a function of the first direction if the first correlation is greater than the second correlation.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An extended field of view is provided for elasticity imaging. This panoramic elasticity image may be useful in clinical practice. Since different frames of elasticity data have different dynamic range due to variation in compression, the elasticity data for each frame may be normalized, minimizing frame-to-frame artifacts in the panoramic image. Since elasticity may be determined from radio frequency data or pre-detection data, the alignment of the frames of data may also be based on radio frequency data. Since elasticity is based on compression or tissue displacement, motion related to extending the field of view may be distinguished from motion related to elasticity imaging. Either real-time or off-line generation is provided.

Figure 1:
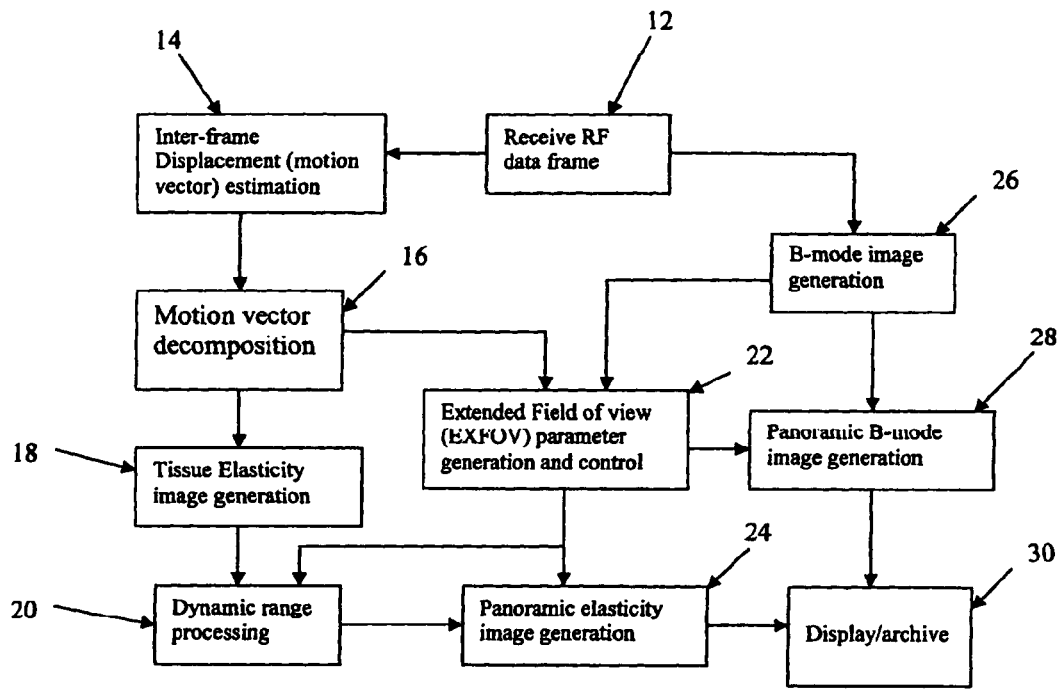
FIG. 1 is a flow chart diagram of one embodiment of a method for panoramic elasticity imaging.

FIG. 1 shows a method for extended field of view ultrasound imaging. Some of the acts may be used for extended field of view B-mode or other modalities of imaging. For example, pre-detection data based alignment or distinguishing between types of motion may be used. In some embodiments, the method is for elasticity ultrasound imaging or generating a panoramic tissue elasticity image. Additional, different or fewer acts may be provided. For example, an elasticity panoramic ultrasound image is generated without generating a B-mode image in act 26 or a panoramic B-mode image in act 28. As another example, the display or archiving act 30 is optional. As another example, the elasticity panoramic image generated in act 24 or the associated supporting acts 16, 18 and 20 are not performed. The acts are performed in the order described or shown, but other orders may be provided.

Figure 2:
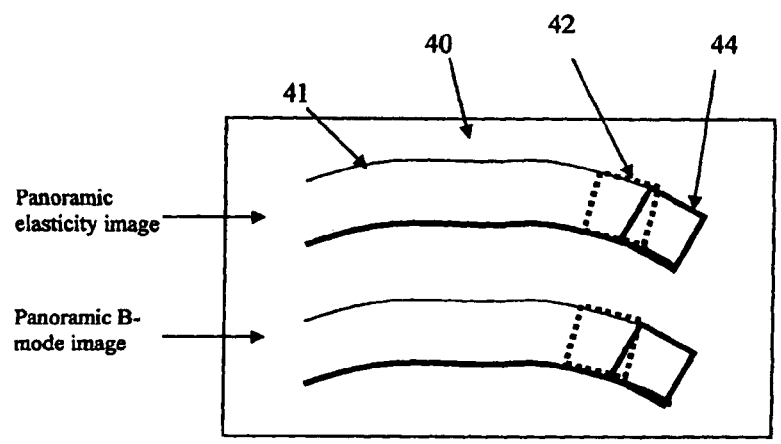
FIG. 2 is a representation of a panoramic elasticity image and two component frames.

In act 12, radio frequency data is received. The data is responsive to ultrasound transmissions and echoes. The radio frequency data is beamformed or represents different spatial locations scanned with ultrasound. For generation of a two or three-dimensional panoramic image, the data corresponds to two or more scans of overlapping but different regions. For example, FIG. 2 shows two component frames of data 42, 44 in panoramic fields of view 41 displayed as an image 40. More than two frames of data may be acquired. FIG. 2 shows the panoramic field of view 41 generated from ten or more frames of data. Frames of data represent two or three dimensional regions or scans, such as associated with a complete scan or the transducer being generally at a same location. For three-dimensional imaging, a plurality of two-dimensional scans may represent the volume. The volume is extended by moving the transducer and scanning the next volume for compositing with the first volume.

The panoramic image 41 is generated from two or more frames of elasticity data representing overlapping but different regions. The elasticity data is information used to estimate stiffness of tissue, such as strain. The data is responsive to compression force or other stress applied to the tissue being scanned. For example, a user applies pressure axially while maintaining a transducer at a lateral location or while translating the transducer laterally. Ultrasound scanning is performed while applying pressure with the transducer against the patient. Alternatively, another source of stress or compression is used, such as acoustic energy or movement within the body.

Where compression force is applied by the transducer, the data for elasticity imaging may be acquired while generally maintaining a lateral position of the transducer, but lateral movement may occur. Axial compression is applied while the ultrasound data is acquired. Upon completion of one or more scans, the transducer is moved from one position to another position. The movement allows for overlapping scan regions, but non-overlapping fields of view may be provided. The movement is manual or by the user, but guided or automated movement may be provided. Referring to FIG. 2, each frame of data 42, 44 represents a different region corresponding to different transducer positions. After moving to the other position, elasticity data is acquired for the current position. Ultrasound scanning is performed again while applying pressure with the transducer against the patient while the transducer is maintained in the current position. This process ends after scanning two regions or may continue for scanning three or more regions.

In act 14, a displacement between frames of data is determined. The displacement is determined along one, two or three dimensions with or without rotation in one, two or three dimensions. FIG. 2 shows one frame of data translated laterally and axially as well as being rotated within the plane of the figure. In one embodiment, the displacement is determined from sensors, such as a magnetic position sensor on the transducer.

In another embodiment, the displacement is determined from ultrasound data. Speckle or features of the patient being scanned may be tracked. For example, an alignment is determined from elasticity data. As another example, the alignment is determined from B-mode or Doppler data. As another example, the radio frequency data or pre-detected data is used to determine the alignment. Pre-detected data may provide more accurate information for the motion vector between frames of data. The alignment provides relative positioning of the frames of data for generating the panoramic image. Any now known or later developed technique for estimating the motion vector or determining the displacement between frames or data may be used, such as any one or more of the techniques disclosed in U.S. Pat. Nos. 5,782,766, 5,910,114, 6,503,201, 6,572,549, 6,730,031, and 6,641,536, the disclosures of which are incorporated herein by reference.

In act 16, the displacement or motion vector is decomposed. A processor distinguishes between moving the transducer in a general lateral direction between different positions and moving the transducer in a general axial direction for acquiring the elasticity data. The general lateral direction corresponds to translation to create the panoramic field of view, and the general axial direction corresponds to the compression force for elasticity imaging. Where the transducer is maintained in a substantially same lateral position for elasticity imaging, then moved to extend the view, and then again maintained in a same position, the processor distinguishes between these events. In an alternative embodiment, the user indicates whether the motion is for imaging or extending the field of view, such as by depressing a button or moving a switch.

In one embodiment, the motion is decomposed into lateral and axial components of the motion vector. A primary displacement between two or more frames of data is determined. The primary displacement is decomposed into lateral and axial displacements. Other directions may be used, such as two or more directions which are not orthogonal or perpendicular to each other.

In another embodiment, direction correlations are computed. Correlations include sum of absolute differences, correlation coefficients or other measures of similarity. The correlation along the different directions is determined. For example, data from two or more frames of data is correlated along a plurality of parallel lines or one dimensionally. An average, mean or other statistic of the directional correlation between the two frames of data is determined.

The directional correlations are compared or used separately. For example, the process continues to act 18 for generation of elasticity imaging if the correlation along the axial axis is larger than the correlation along the lateral axis. The process continues to act 22 for defining the extended field of view if the correlation along the lateral axis is larger than the correlation along the axial axis. As another example, the directional correlations are both used, but for the different acts 18, 22. As another example, the axial motion or correlation is used for generating elasticity data in act 18 and both axial and lateral motion are used for defining the extended field of view in act 22. One, two or three-dimensional motion may be used for elasticity or extended field of view. The same or different motions are provided for the different acts.

In act 18, axial motion is used to generate elasticity data, such as a frame of data representing the elasticity of tissue. Elasticity or elastography are general terms that include various types of parametric images of tissue stiffness, such as strain, strain rate, modulus or relaxation, and various methods of mechanically generating them. Strain images show tissue relative stiffness and deformation. Strain rate images display the first time derivative of the strain. Local strain rate may indicate cardiac muscle contractility from which is inferred the muscle health and condition. Modulus images (e.g., Young's modulus) may be generated when the strain image or strain rate image is normalized by and combined with stress measurements. One method is to measure the pressure at the body surface with sensors attached to the transducer. The stress field pattern is then extrapolated internally to the points (i.e., pixels or voxels) of measured strain. Young's modulus is defined as stress divide by strain. Local modulus values may be calculated and those numerical values are converted to gray scale or color values for display. In strain imaging, local 1D, 2D, or 3D displacements are measured and the numerical displacement values are converted to gray scale or color values for display.

Strain images may be generated with manual palpation, external vibration sources, inherent tissues motion (e.g., motion due to cardiac pulsations, or breathing) or acoustic radiation force imaging (ARFI). ARFI produces strain images or produces relaxation images. Relaxation images may be displayed parametrically in similar fashion to strain and modulus images. The parametric images are generated with one (e.g., M-mode), two (e.g., B-mode), three (e.g., static volumetric), or four (e.g., dynamic volumetric) dimensional acquisition and imaging. In one embodiment, any one or more of the methods or systems disclosed in U.S. Pat. Nos. 5,107,837, 5,293,870, 5,178,147, 6,508,768 or 6,558,324, the disclosures of which are incorporated herein by reference, are used to generate elasticity frames of data or images.

Figure 3:
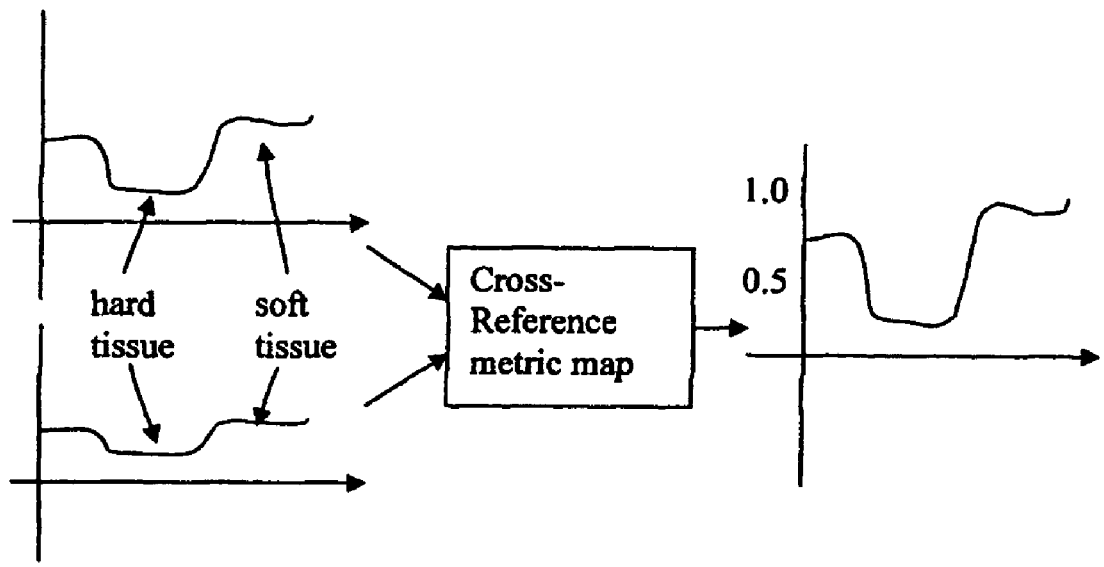
FIG. 3 is a graphical representation of updating the dynamic range of component frames of data for panoramic display.

In act 20, the dynamic range of the elasticity data is updated to avoid frame-based artifacts in the panoramic elasticity image 41. Each frame of elasticity data may be a result of different compressions, changes in compression or other elasticity parameters. The upper and lower graphs on the left of FIG. 3 show lines of data representing a same region but with different amplitudes. The different amplitudes result from different amounts of compression being applied when acquiring the data. For the same tissue profile, two strain profiles generated under two different compression force changes result in different dynamic ranges. Since strain is a relative value, its number may not give easily used diagnosis information without knowing the stress.

To overcome the implicit drawback of the strain imaging, the dynamic range of the elasticity data is updated. In most elasticity imaging applications, the field of view of each strain image includes normal soft tissue, such as breast fat tissue, that can be used as the reference. The normal softest tissue has the highest strain in the field of view as compared with other normal and pathological tissue. According to Hook's law, the strain is linearly proportional to the stress. This linear relationship is valid when the compression is small. The compression is small in practical applications for ultrasound. The ratio of the strain in different tissues as a metric holds relatively constant although the strain values may vary under different compression force.

To update the dynamic range, each frame of elasticity data is normalized using the highest strain value from the frame of data. Alternatively, the normalization uses the elasticity data from the extended field of view to determine a normalization value. For example, the maximum value of strain is $E_{max}$. For each pixel (x,y), a strain $e(x, y)$ is determined. $p(x, y)$ is the percentage calculated as $e(x, y)$ divided by $E_{max}$. The color-coding or data used for imaging is based on the percentage value $p(x, y)$, and the range of the color-coding is $[\alpha, 1]$. The percentage is mapped between $\alpha$ and 1. A value of 1 is the normal and most transparent in color, and a value of $\alpha$ is the most hard and red in color. The value $\alpha$ may be determined empirically from a set of pathological data. FIG. 3 shows normalization or updating the dynamic range as a cross reference metric map.

After normalization, each frame of data has a similar dynamic range. In act 24, a panoramic elasticity image is generated as a function of the normalized elasticity frames of data. In act 22, the extended field of view parameters and control are generated. The parameters include determining the alignment or overlap from the displacement. The control determines whether overlapping data is discarded or combined with previous data. Filter parameters for combination may be selected. Data representing newly scanned spatial locations is identified and assigned to the appropriate locations on the extended field of view image. Where the dynamic range processing of act 20 is performed as a function of data selected for the extended field of view image or other extended field of view parameters, the information is used in act 20. Another parameter includes mapping or combination selection for the elasticity and other types of data. For example, a color map is selected for elasticity data and a gray scale map is selected for B-mode data. A common map outputting display values for a linear or nonlinear combination of elasticity and other data may be provided.

Whether to display the elasticity data may also be controlled in act 22. Out of plane or rapid axial or lateral movement may result in incorrect elasticity estimation. In a real-time or live scan, the user may move the transducer from place to place while investigating the region of interest. When the movement occurs, the resulting elasticity measurements may be noise that covers much or the entire associated image. To suppress noise, flash suppression is used. In one embodiment, the noise suppression is based on an amount of decorrelation between frames of data. The decorrelation is measured as the direction correlation from one or more directions used in act 16, or a different correlation, such as a multidimensional correlation between two or more frames of data. In one embodiment, localized correlation is determined, such as determining a correlation for each or a sub-set of the pixel or voxel locations. A global or general correlation is determined from the local correlations. A mean or variance of correlation from the localized correlations is calculated. For example, a first or second moment from a histogram of the correlations indicates mean and variance, respectively. A map for the image or image values are selected as a function of the amount of correlation. If the correlation is above a threshold value, the elasticity data is used. If the correlation is below a threshold value, B-mode data is used without elasticity data. Multiple levels of thresholds may be used, such as varying amounts of emphasis of elasticity data relative to B-mode data. The threshold may adapt, such as changing in value based on the imaging application or ultrasound data.

In act 24, an image representing two or more different regions of the patient is generated. The image is a panoramic elasticity image. The elasticity data is mapped to display values. Panoramic imaging is the generation of fields of view larger than a single image by correlating successive 2D images or 3D volumes and combining them into one composite display. Panoramic imaging may more likely place local tissue lesions and features into overall anatomical context and more likely provide reference for surgeons, referring physicians, the patient, or the lay public. As a continuing sequence of elasticity frames of data and associated regions are obtained or provided, the extended field of view image is extended. Alternatively, the image is not displayed until complete.

The panoramic elasticity image is displayed alone. Alternatively, a B-mode or other image representing the same extended field of view or a different field of view is displayed adjacent to the panoramic elasticity image. In another alternative embodiment, the elasticity image is combined with or overlaid on the B-mode image.

In act 26, the same or different radio frequency data from act 12 is detected. B-mode intensities are detected, but other imaging modes may be used. The B-mode data may be used for determining extended field of view parameters or control. In act 28, a panoramic B-mode image is generated.

In act 30, the panoramic tissue elasticity image is displayed or stored. For storage, elasticity data other than display values may be stored. Similarly, B-mode or other imaging data is displayed or stored. Component frames of data used to form the extended field of view may be alternatively or additionally stored.

Figure 4:
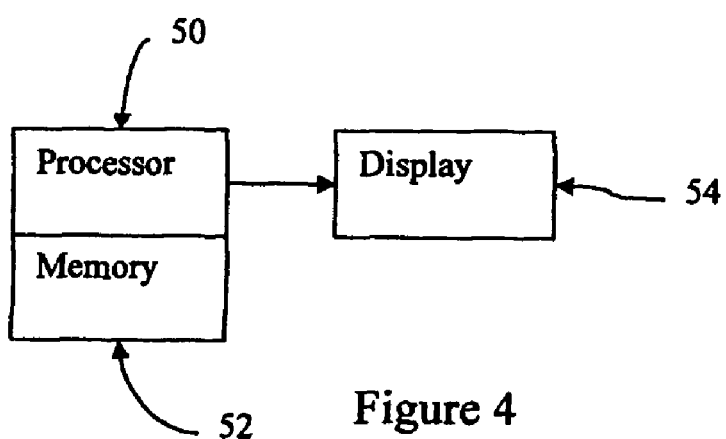
FIG. 4 is a block diagram of one embodiment of a system for panoramic elasticity imaging.

FIG. 4 shows one embodiment of a system for speckle adaptive medical image processing. The system implements the method of FIG. 1 or other methods. The system includes a processor 50, a memory 52, and a display 54. Additional, different or fewer components may be provided. For example, a user input is provided for manual or assisted selection of extended field of view parameters or other control. As another example, the system is a medical diagnostic ultrasound imaging system that also includes a beamformer and a transducer for real-time acquisition and imaging. Other medical imaging systems may be used. In another embodiment, the system 60 is a personal computer, workstation, PACS station or other arrangement at a same location or distributed over a network for real-time or post acquisition imaging.

The processor 50 is a control processor, general processor, digital signal processor, application specific integrated circuit, field programmable gate array, network, server, group of processors, data path, combinations thereof or other now known or later developed device for estimating elasticity, determining extended field of view parameters, identifying motion vectors, updating dynamic range, decomposing motion vectors or other acts. For example, the processor 50 or a data path of processors including the processor 50 detects B-mode data, generating B-mode images and generates an extended field of view B-mode image. As another example, the processor 50 or a data path including the processor 50 performs any combination of one or more of the acts shown in FIG. 1.

The processor 50 operates pursuant to instructions stored in the memory 52 or another memory. The processor 50 is programmed for extended field of view ultrasound imaging, such as programmed to generate a panoramic tissue elasticity image.

The memory 52 is a computer readable storage media. The instructions for implementing the processes, methods and/or techniques discussed above are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The memory 62 may store alternatively or additionally ultrasound data for generating images. The ultrasound data is the radio frequency data, elasticity data or B-mode data, but may include alternatively or additionally data at different stages of processing.

The display 54 is a CRT, LCD, projector, plasma, or other display for displaying two-dimensional panoramic images, or three or four-dimensional panoramic representations.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for elasticity ultrasound imaging, the method comprising:

acquiring first elasticity data with ultrasound for a first region corresponding to a first position of a transducer, the first elasticity data representing tissue stiffness in the first region derived from first axial motion between a first group of at least two frames of data;

moving the transducer from the first position to a second position, displacing a location in which to acquire elasticity data;

acquiring second elasticity data with ultrasound for a second region corresponding to the second position of the transducer, the second position and second region different than the first position and first region due to the moving, respectively, the second elasticity data representing tissue stiffness in the second region and derived from second axial motion between a second group of at least two frames of data;

distinguishing with a processor between moving the transducer in a general lateral direction from the first position to the second position and moving the transducer in a general axial direction for acquiring the first or second elasticity data;

updating the dynamic range of at least the first elasticity data; and generating an image representing both first and second regions, the image being a function of the first and second elasticity data.

2. The method of claim 1 wherein acquiring the first elasticity data comprises scanning while applying pressure with the transducer against a patient while the transducer is maintained in the first position and wherein acquiring the second elasticity data comprises scanning while applying pressure with the transducer against the patient while the transducer is maintained in the second position.

3. The method of claim 1 wherein distinguishing comprises:

determining a primary displacement between two or more frames of data;

decomposing the primary displacement into lateral and axial displacements;

combining the two or more frames in an extended field of view if the lateral displacement is greater than the axial displacement; and generating the first or second elasticity data if the axial displacement is greater than the lateral displacement.

4. The method of claim 1 wherein distinguishing comprises:

determining a first correlation between two or more frames of data in the lateral direction;

determining a second correlation between the two or more frames of data in the axial direction;

combining the two or more frames in an extended field of view if the first correlation is greater than the second correlation; and generating the first or second elasticity data if the second correlation is greater than the first correlation.

5. The method of claim 1 wherein generating comprises determining an alignment of the first elasticity data with the second elasticity data as a function of B-mode data, and generating the image as a function of the alignment.

6. The method of claim 1 wherein generating comprises determining an alignment of the first elasticity data with the second elasticity data as a function of pre-detected data, and generating the image as a function of the alignment.

7. The method of claim 1 wherein updating comprises:

normalizing the first elasticity data; and normalizing the second elasticity data;

wherein generating the image comprises generating the image as a function of the normalized first and second elasticity data.

8. The method of claim 1 further comprising:
   determining an amount of correlation between frames of data;
   selecting a map for the image as a function of the amount of correlation.

9. The method of claim 8 wherein determining the amount of correlation comprises determining a mean or variance of correlation between the frames of data, and wherein selecting a map comprises mapping the first and second elasticity data to the image where the amount of correlation is above a threshold and mapping B-mode data where the amount of correlation is below the threshold.

* * * * *